United States Patent [19]

Garcea et al.

[11] 4,308,519
[45] Dec. 29, 1981

[54] DEVICE FOR DETECTING THE KNOCKING PHENOMENON IN CONTROLLED-IGNITION INTERNAL COMBUSTION ENGINES, BASED ON THE USE OF IONIZATION PROBES

[75] Inventors: Giampaolo Garcea; Edoardo Rogora, both of Milan, Italy

[73] Assignee: Alfa Romeo S.p.A., Milan, Italy

[21] Appl. No.: 63,567

[22] Filed: Aug. 3, 1979

[30] Foreign Application Priority Data

Aug. 11, 1978 [IT]  Italy ................ 26739 A/78

[51] Int. Cl.³ .............. F02B 77/08; G08B 21/00
[52] U.S. Cl. ............................ 340/53; 60/277; 123/198 A; 340/57; 340/579; 340/588
[58] Field of Search .......... 340/52 R, 53, 60, 57, 340/579, 588; 123/119 E, 198 A, 347, 381, 425; 60/277, 286; 364/431, 442

[56] References Cited

U.S. PATENT DOCUMENTS

| 2,306,372 | 12/1942 | Banks | 340/60 |
| 2,404,569 | 7/1946 | Eldredge et al. | 340/60 X |
| 2,517,976 | 8/1950 | Clarke | 340/579 |
| 3,576,526 | 4/1971 | Arnold et al. | 340/52 R |
| 3,908,366 | 9/1975 | Masaki | 340/579 X |

Primary Examiner—John W. Caldwell, Sr.
Assistant Examiner—Joseph E. Nowicki
Attorney, Agent, or Firm—Charles E. Brown

[57] ABSTRACT

A device is disclosed which detects the knocking phenomena in a controlled-ignition internal combustion engine, the device essentially comprising two ionization probes arranged in a zone of the explosion chamber remote from the sparking plug: the probes deliver signals when the state of ionization changes and the time interval between the signals of the two probes is measured and compared with an appropriate reference value.

8 Claims, 3 Drawing Figures

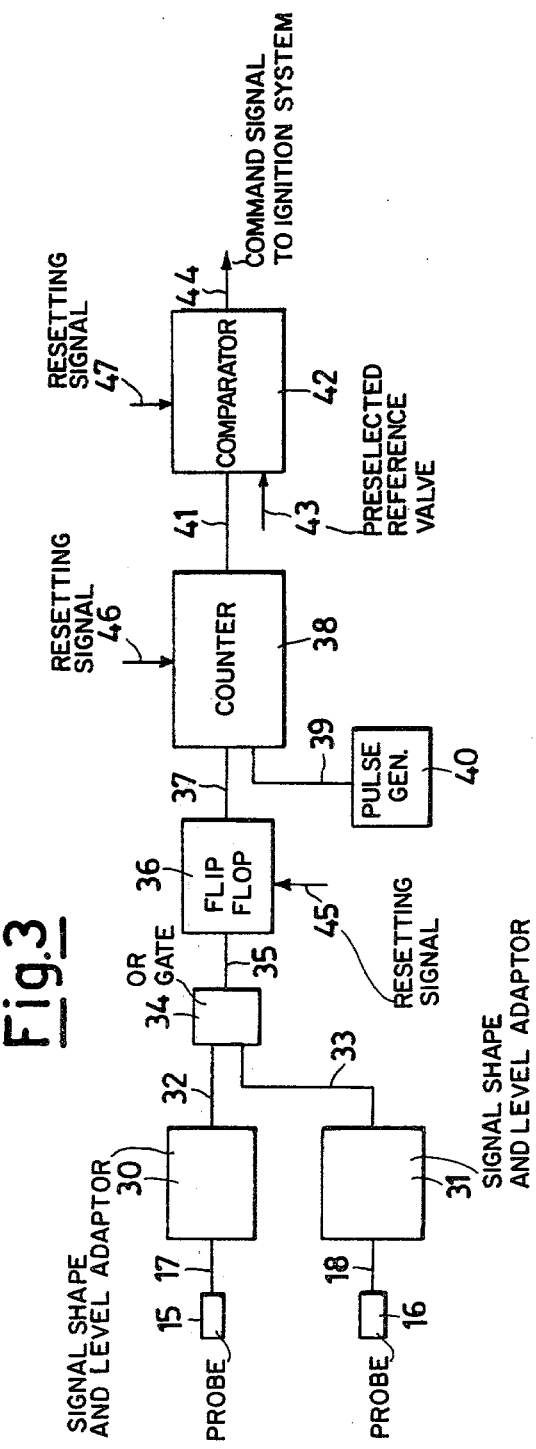

DEVICE FOR DETECTING THE KNOCKING PHENOMENON IN CONTROLLED-IGNITION INTERNAL COMBUSTION ENGINES, BASED ON THE USE OF IONIZATION PROBES

There have been suggested and manufactured devices for detecting the knock phenomenon, which essentially use signals coming from sensors of vibratory phenomena at high frequency which accompany knocking. The device according to the present invention, conversely, intends to discriminate the regular combustion of the mixture from the anomalous combustion originated by the knocking phenomenon by exploiting the signals coming from ionization probes, that is to say ionization probes arranged in the interior of the explosion chamber. The principle on which the device is based is connected with the different mode of propagation of the flames in the two cases aforementioned. As a matter of fact, due to the effect, above all, of the compression which occurs during the compression stroke of the piston and then due to the effect of the increase of volume and thus of pressure of the portion of the mixture which is gradually burned as the flame front proceeds, the portion of mixture which is burned the last is considerably compressed prior to burning. The pressure increase is obviously accompanied by a considerable increase of temperature of that portion of the mixture since both the successive phases of compression aforesaid may be considered as adiabatic compression or even compressions with administration of heat on account of the high temperatures of the walls and the irradiation by the already burned gas. It is likewise known that if the gasoline has inadequate antiknock protection (consistently with the values of pressure and temperature attained by the portion of the mixture which burns last) the combustion takes place in the same instant of time for all the points of the mixture which have not yet been burned: in that zone of the chamber, which is more or less extended according to whether the knocking phenomenon is more or less intense, no regular combustion is experienced by propagation of the flame front, but an explosion proper. Inasmuch as the electric conductivity of the dielectric composed by the burned gas having a high temperature is much higher than that of the dielectric composed by the unburned mixture, a ionization probe arranged in the interior of the explosion chamber may give a signal in the instant of time of the combustion.

It has thus been envisaged to place in the explosion chamber two probes, both arranged in the zone, generally the most remote from the sparking plug, in which the mixture burns last: a zone which is thus typical for incipient knocking. These two probes in addition are situated at a certain distance from one another in the direction along which the flame front of the regular combustion proceeds. When the combustion is regular the two signals corresponding to the sudden ionization rise are thus supplied by the probes with a certain time interval from one another: for example, if the distance between the two probes is one centimeter and the velocity of advance of the flame front is 20 meters a second, this time interval is 500 microseconds. When, conversely, the combustion is anamalous due to knocking in progress, in the zone encompassing the two probes the aforementioned two signals corresponding to the ionization increase are emitted simultaneously or, at any rate, with a time interval which is considerably shorter than that of the previous case. According to the present invention, the two signals are delivered to an electronic circuit equipped with means capable of detecting the time interval which separates the two and of comparing it with a threshold value in order to assess if the former is longer or shorter than the latter. In the former case the combustion is regular and in the latter knocking is in progress.

According to a first embodiment of the device according to the present invention provision is made that the electronic circuit is connected to a signalling means, preferably luminous, arranged on the dashboard in front of the driver's seat, so that in the second of the cases discussed above, that is when knocking is in progress, the signal warns the driver of the existence of knocking and can thus reduce the power delivery by the engine until the signal warns him that knocking is over. According to an alternative embodiment, provision is made so that the electronic circuit aforesaid is equipped with means operatively connected to the ignition system of the engine and capable of generating a command for decreasing the ignition advance relative to the basic adjustment of the ignition system which determines such advance as a function of at least one of the engine parameters, the engine RPM for example.

By so doing, in the second of the cases discussed in the foregoing, that is when knocking is experienced, the electronic circuit delivers a command for a quick reduction of the advance of ignition relative to the basic adjustment, and this command lasts until the time interval between the two signals returns to be longer that the threshold value aforesaid. On bearing in mind, then, the circumstances that while the device enters action to reduce the ignition advance the engine parameters aforementioned of the basic adjustment may change, for example the engine RPM, among the various versions of the device the one which is preferred is the one according to which the command for the reduction of the ignition advance involves the entire basic adjustment and not only the point of that adjustment which corresponds to the parameters which are valid in the instant of time in which knocking has been detected. Then to avoid that, as a result of a considerable variation of said parameters, or anyhow of the degree of use of the engine (for example when passing to the use of the vehicle to constant speed conditions after an acceleration), the reduction of the ignition advance is continued also when it is no longer necessary, other means are provided which are capable of carrying out a gradual annulment, within a sufficiently narrow time interval, of the reduction of the ignition advance, and this is made starting from the instant of time at which the reduction has been introduced. It is obvious that, if during such gradual annulment, the knocking phenomenon appears again, a new command starts from the device to suppress it once more.

FIG. 3 is a block diagram of a preferred embodiment of the electronic circuit shown in FIG. 1.

Figure 1:
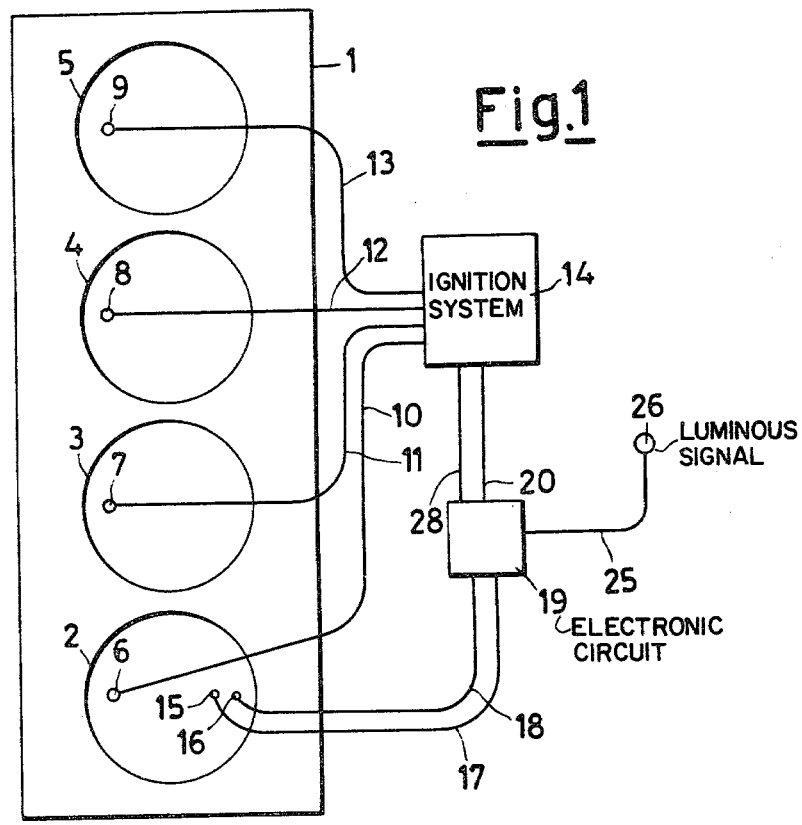
FIG. 1 is a schematic view of the overall configuration of the detector in a controlled-ignition internal combustion engine in accordance with the present invention.

In order that the foregoing may be better understood, FIG. 1 of the accompanying drawings indicates diagrammatically at 1 the engine block (in the example shown it is an in line 4-cylinder engine) viewed along the direction of the cylinder axis, at 2, 3, 4 and 5 the cylinders, st 6, 7, 8 and 9 the sparking plugs of said cylinders, at 10, 11, 12 and 13 the ignition cables which lead the ignition current to the plugs, at 14 the ignition system which delivers the current to the plugs with a determined basic adjustment of the ignition advance relative to the upper dead center of the pistons corresponding to the various cylinders, at 15 and 16 the two ionization probes arranged in the explosion chamber of the cylinder indicated at 2, said probes being sufficiently near one another and aligned with the plug 6 so that the flame front starting from the plug 6 impinges, when going on, first on the probe 15 and then on the probe 16 in the case of regular combustion, both the probes being located in the zone of the chamber which is farthest from the plug, as this zone is generally that in which incipient knocking occurs. In addition, there are shown at 17 and 18 the electric connections of the two probes with an electronic circuit, 19, which processes the signals coming from the two probes and detects the time interval which separates the signal from the probe 15 from the one delivered by the probe 16 and compares said interval with a reference time interval having a preselected magnitude in order to assess if the former is longer or shorter than the latter.

The line 28 stemming from the system 14 supplies the circuit 19 with a resetting signal generated by the ignition signal delivered to the cylinder which, in the ignition sequence, is immediately before the cylinder 2. Said resetting signal presets the circuit 19 to detecting the knocking in the same cylinder 2 at every engine cycle.

According to a first embodiment of the device in question the electronic circuit is capable of delivering a command to the warning means 26 (which is for example a luminous signal arranged on the dashboard) through the connection 25. According to an alternative embodiment, instead, the electronic circuit is capable of delivering, on the basis of that evaluation, a possible command to the ignition system 14 via the electric connection 20, for example to carry out a gradual rapid decrease of the advance relative to what had been preset by the basic adjustment of the system 14.

In the system 14 there can be provided other means which are capable of cutting off the command for the quick and gradual decrease of the advance as soon as the time interval between the signals of the two probes 15 and 16 is longer than a second preselected value which can either be, in its turn, equal to or longer than said first preselected value. Further means can be provided, moreover, which, at the instant of time at which the command for the quick and gradual decrease of the advance, are capable of commanding a less rapid gradual increase of the advance in order to bring it back towards the values of the basic regulation.

This temporary correction of the advance relative to the basic adjustment can be carried out along the entire advance curve and thus along the entire field of operation of the engine, or in a few zones of that field on-ly.

Figure 2:
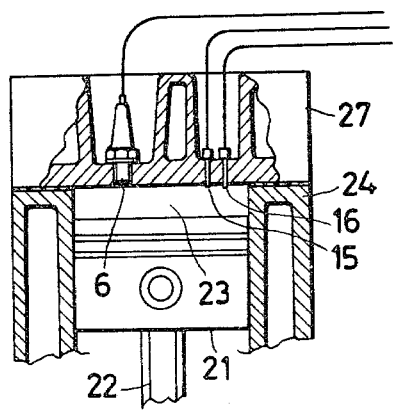
FIG. 2 is a cross-sectional view of the head and the cylinder shown in FIG. 1.

FIG. 2, moreover, shows a diagrammatical cross-sectional view of the head and the cylinder indicated at 2 in FIG. 1, said fragmentary cross-section being taken along a plane parallel to the cylinder axis and passing through the straight line which conjoins the spark plug 6 with the probes 15 and 16; in this Figure, 21 indicates the piston and 22 the connecting rod, both in the position corresponding to the upper dead center, and 23 is the explosion chamber into which the spark plug 6 and the two probes 15 and 16 project. At 24 there is shown the cylinder block and at 27 the engine head.

FIG. 3 shows a block diagram of a preferred embodiment of the electronic circuit 19 of FIG. 1.

There are indicated at 30 and 31 two signal shape and level adaptors, which are respectively connected to the ionization probe 15 via the line 17, and to the ionization probe 16 via the line 18.

These adaptors are connected with the respective outputs 32 and 33 to a logical unmatching gate of the OR type indicated at 34, the output 35 of which is connected to the input of a flip-flop indicated at 36. The output 37 of the flip-flop 36 is connected to one input of a counter, indicated at 38, which receives also the signal 39 composed by a train of constant-frequency pulses, delivered by pulse generator indicated at 40. The output 41 of the counter 38 is connected to one input of a comparator indicated at 42, which also receives the signal 43 composed by a preselected reference value.

The output 44 of the comparator 42 is to be connected to the lines 20 and 25 shown in FIG. 1.

There are indicated, at 45, 46 and 47, resetting signals which come from the line 28 of FIG. 1, to the flip-flop 36, the counter 38 and the comparator 42, respectively. Such resetting signals are generated by an ignition signal delivered by the ignition system 14 of FIG. 1 to the cylinder which, in the ignition sequential order precedes the cylinder 2 equipped with the probes 15 and 16.

The ionization signal emitted by the probe 15 when the mixture which is present in its interior burns, is converted in the adapter 30 and sent through the line 32 and the gate 34 to the flip-flop 36, which is switched to its second stable state and commands the counter 38 to start the counting of the constant-frequency pulses which compose the signal 38.

The ionization signal delivered by the probe 16 when the mixture which is present in its interior burns, is converted in the adaptor 31 and delivered via line 33 and gate 34 to the flip-flop 36: the latter is switched to its first stable state and commands the counter 38 to stop counting the constant-frequency pulses.

The number of pulses counted by counter 38 in the time interval which elapsed between the ionization signals delivered by the two probes 15 and 16 is sent to the comparator 42 wherein it is compared with the signal which represents the preselected reference value.

If the number of the counted up pulses is greater than the reference value, the comparator 42 does not deliver any signals at its own output 44 because this fact means that the time interval between the signals of the two probes 15 and 16 is in order and is due to the normal advance of the flame front in the combustion chamber of the cylinder 2.

If, on the contrary, the number of summed up pulses is smaller than the reference value, at the output 44 of the comparator 42 a signal appears which indicates the existence of an anomalous time interval between the signals of the two probes 15 and 16 due to the occurrence of knocks in the combustion chamber of the cylinder 2.

We claim:

1. A device for detecting the knocking phenomenon in a controlled-ignition internal combustion engine equipped with an ignition system for effecting electrical discharge to spark plugs of said engine with a preselected basic adjustment of ignition advance relative to the upper dead center of the various engine pistons, said device being capable of detecting the possible occurrence of the knocking phenomenon in the explosion chamber of at least one of the engine cylinders, said device comprising at least two ionization probes both arranged in said chamber in a zone generally the farthest from the spark plug where the incipient knocking phenomenon normally occurs, said two probes being furthermore positioned comparatively apart from one another essentially along the direction of propagation of a flame front from the associated spark plug, and further comprising an electronic circuit which receives signals coming from said two probes, said circuit including means for detecting the time interval existing between the two signals and for comparing said time interval with a threshold interval to assess if the detected time interval is longer than the threshold interval, to discriminate if the combustion is regular or is not due to the occurrence of knocking phenomena.

2. A device according to claim 1, characterized in that said electronic circuit is also connected to a warning means which is preferably a pilot lamp placed on the dashboard in front of the driver's seat in order to warn the driver of the possible occurrence of knocking phenomena.

3. A device according to claim 1, characterized in that said electronic circuit is also equipped with means connected to said ignition system and capable of generating, in the case in which the time interval is shorter that the preselected value, a command for a decrease of the ignition advance relative to the value corresponding to the preselected basic adjustment.

4. A device according to claim 1, characterized in that the electronic circuit also comprises other means which are capable of commanding, in the case in which the time interval between the two signals is shorter than the preselected value, a quick gradual decrease of the ignition advance relative to the value corresponding to the preselected basic adjustment and capable of arresting the gradual reduction of the advance as soon as the interval between the two signals becomes longer than a further preselected value which is somewhat higher than or also equal to said first named preselected value.

5. A device according to claim 3 or claim 4, characterized in that said circuit is capable of sending to the ignition system the command for decreasing the ignition advance relative to the value corresponding to the preselected basic adjustment in at least one zone of the field of such basic adjustment.

6. A device according to claim 5, characterized in that the electronic circuit comprises further means which are capable, at the instant of time at which said command is discontinued, of stopping the quick gradual reduction of the advance and of starting to command a less rapid gradual increase of the ignition advance towards the value corresponding to the preselected basic adjustment.

7. A device according to claim 4 characterized in that the electronic circuit comprises further means which are capable, at the instant of time at which said command is discontinued, of stopping the quick gradual reduction of the advance and of starting to command a less rapid gradual increase of the ignition advance towards the value corresponding to the preselected basic adjustment.

8. A device according to claim 1, characterized in that said electronic circuit comprises a counter which receives a constant-frequency pulse train delivered by a pulse generator, said counter being operatively connected to said probes for being commanded by a signal delivered by either probe to start the counting of the constant-frequency pulses and for being commanded by the signal delivered by the other probe to stop the counting of such pulses, the circuit also comprising a comparator which receives a preselected reference value, the comparator being connected to said counter to compare the signal formed by the pulses summed by said counter with said reference value, the comparator delivering a signal which indicates the occurrence of knocking when the number of the summed pulses is less than the reference value.

* * * * *